(12) United States Patent
Doki

(10) Patent No.: US 6,306,410 B1
(45) Date of Patent: Oct. 23, 2001

(54) COSMETIC FORMULATIONS CONTAINING ETHOXYLATED PARTIAL GLYCERIDES

(75) Inventor: Kakushi Doki, Tokyo (JP)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/509,382

(22) PCT Filed: Sep. 15, 1998

(86) PCT No.: PCT/EP98/05839

§ 371 Date: Jun. 1, 2000

§ 102(e) Date: Jun. 1, 2000

(87) PCT Pub. No.: WO99/15146

PCT Pub. Date: Apr. 1, 1999

(30) Foreign Application Priority Data

Sep. 24, 1997 (JP) .................................. 9-258951

(51) Int. Cl.[7] .................................. A61K 7/00; A61K 7/42
(52) U.S. Cl. .................................. 424/401; 424/59
(58) Field of Search ....................... 424/401, 59

(56) References Cited

U.S. PATENT DOCUMENTS

| | | | |
|---|---|---|---|
| 3,934,003 | * | 1/1976 | Tuma et al. .................. 424/59 |
| 4,172,887 | | 10/1979 | Vanlerberghe et al. ......... 424/70 |

FOREIGN PATENT DOCUMENTS

| | | |
|---|---|---|
| 1 165 574 | 3/1964 | (DE) . |
| 20 24 051 A | 12/1971 | (DE) . |
| 208 558 A | 4/1984 | (DE) . |
| 42 43 119 A1 | 6/1994 | (DE) . |
| 195 25 108 A1 | 1/1997 | (DE) . |
| 2 252 840 | 8/1975 | (FR) . |
| 962919 | 7/1964 | (GB) . |
| 63/122618 | 5/1988 | (JP) . |
| 04/005213 | 1/1992 | (JP) . |
| 07/215840 | 8/1995 | (JP) . |
| 07/215842 | 8/1995 | (JP) . |
| 07/291831 | 11/1995 | (JP) . |
| 07/304630 | 11/1995 | (JP) . |

OTHER PUBLICATIONS

P. Finkel, SÖFW–Journal, 122, (Aug., 1996), pp. 543–546 & 548.

"Kosmetische Färbemittel", Farbstoffkommission der Deutschen Forschungsgemeinschaft, Verlag Chemie, Weinheim, (1984), pp. 81–106.

* cited by examiner

Primary Examiner—Shelley A. Dodson
Assistant Examiner—Konata M George
(74) Attorney, Agent, or Firm—John E. Drach; Aaron R. Ettelman

(57) ABSTRACT

Cosmetic formulations, such as for example, skin cleansers, containing from about 20% to about 80% by weight of one or more ethoxylated partial glycerides of the general formula (I) and up to about 80% by weight of an oil component, the balance of the formulations containing water, cosmetic auxiliaries and/or additives, are disclosed. The cosmetic formulations disclosed are transparent, and spread easily and smoothly when applied to skin. Such formulations are especially suitable for removing decorative makeup.

20 Claims, No Drawings

COSMETIC FORMULATIONS CONTAINING ETHOXYLATED PARTIAL GLYCERIDES

BACKGROUND OF THE INVENTION

Oilbased decorative cosmetics, such as lipstick, foundation, mascara or eye shadow, are normally removed from the skin by a two-stage procedure. First, greasy skin soils are removed with massage creme, cleansing creme, cleansing oil, cleansing gel and/or other face washes which combine well with decorative cosmetics. In a second step, greasy residues remaining on the skin, tallow and other soils are washed off with soap or cleansing foams. This two-stage cleansing of the skin is necessary because, where formulations containing oil components in relatively large amounts (for example massage cremes) are used, the oil components remaining on the skin cannot be sufficiently removed by subsequent rinsing with cold or luke-warm water, so that no feeling of freshness can be imparted to the skin. If, by contrast, washing formulations alone, such as soaps, are used to cleanse the skin, pigments and other coloring substances surrounded by oil components cannot be removed. In recent years, however, there has been a demand for easy-to-use cosmetics and make-up removers which are capable of removing decorative cosmetics in a single wash and of imparting a fresh, non-greasy "washed" feeling. Corresponding one-step formulations are known, for example, from JP-A Sho 63/122618, JP-A Hei 04/005213 and JP-A Hei 07/215842. These formulations are single-phase or two-phase face washes which contain certain nonionic surfactants in combination with water-soluble substances. In addition, foaming washes based on certain nonionic surfactants and anionic surfactants are known from JP-A Hei 07/215840, JP-A Hei 07/304630 and JP-A Hei 07/29/831. Unfortunately, these one-step face washes are still unsatisfactory in two respects. First, they have a poor skin-cleansing effect with respect to decorative cosmetics which, in recent years, have contained increasing levels of oil components or even film formers. Second, the sensorial impression which they impart, for example as regards spreading or slip on application to the skin, is in need of improvement.

Reference is also made in this connection to DE 2024051 C3 (Henkel) which describes the use of ethoxylated partial glycerides as refatting agents.

Accordingly, the problem addressed by the invention was to provide cosmetic formulations, particularly skin cleansers, which would cleanse the skin in one step and, in doing so, would completely remove cosmetics, particularly decorative cosmetics, for example make-up, eye shadow, rouge, kajal, mascara, lipstick and the like. For aesthetic reasons, the formulations would be single-phase, transparent and low-viscosity formulations and would not lose these properties, even in the event of storage at relatively high temperatures. Finally, the formulations would leave behind a sensorially agreeable light feeling.

BRIEF SUMMARY OF THE INVENTION

The present invention includes cosmetic formulations having a defined nonionic surfactant content, for example, skin cleansers for removing decorative cosmetics.

(a) 20 to 80 and preferably 25 to 35% by weight of ethoxylated partial glycerides and optionally (b) 0.1 to 80 and preferably 15 to 75% by weight of oils, with the proviso that the quantities add up to 100% by weight, optionally with water and typical auxiliaries and additives.

It has surprisingly been found that formulations of the type mentioned above comprise one phase and are transparent. The single-phase character of the formulations according to the invention emanates from the fact that they are not o/w or w/o emulsions, but transparent or semi-transparent compositions. They have a sufficient, but not excessive viscosity for application which they retain, even in the event of storage at relatively high temperatures. The invention includes the observation that the formulations are easy to rinse off with water, completely remove decorative cosmetics, more particularly make-up, mascara and eye shadow, in one step and, at the same time, impart a pleasant feeling to the skin.

DETAILED DESCRIPTION OF THE INVENTION

Ethoxylated partial glycerides, i.e. addition products of ethylene oxide with monoglycerides, diglycerides and technical mixtures thereof, can contain small quantities of triglycerides from their production. The partial glycerides preferably correspond to formula (I):

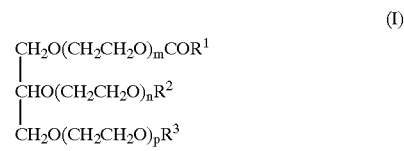

where $R^1CO$ is a linear or branched, saturated and/or unsaturated acyl group containing 6 to 22 and preferably 12 to 18 carbon atoms, $R^2$ and $R^3$ independently of one another have the same meaning as $R^1CO$ or represent OH and the sum $(m+n+p)$ is a number of 1 to 100 and preferably 5 to 10, with the proviso that at least one of the two substituents $R^2$ and $R^3$ is OH. Typical examples are addition products of 5 to 10 moles of ethylene oxide with mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Technical ethoxylated lauric acid glycerides, palmitic acid glycerides, stearic acid glycerides, isostearic acid glycerides, oleic acid glycerides, behenic acid glycerides and/or erucic acid glycerides with about 7 moles of ethylene oxide, which have a monoglyceride content of 50 to 95 and preferably 60 to 90% by weight, are preferably used.

Oils

Suitable oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/ di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic add with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons.

Cosmetic Formulations

The formulations according to the invention, for example cremes, lotions or emollients, may additionally contain mild surfactants, emulsifiers, superfatting agents, pearlescing waxes, stabilizers, consistency regulators, thickeners, polymers, silicone compounds, biogenic agents, anti-dandruff agents, film-formers, preservatives, hydrotropes, solubilizers, UV filters, insect repellents, self-tanning agents, perfume oils, dyes and the like. The formulations are suitable not only for cleansing the skin, but also for caring for and protecting the skin. Accordingly, possible embodiments of the invention also include the use of the formulations for the production of make-up removers and sun blocks.

Typical examples of suitable mild, i.e. dermatologically compatible, surfactants are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, ether carboxylic acids, alkyl oligoglucosides, fatty acid glucamides, alkyl amidobetaines and/or protein fatty acid condensates (preferably based on wheat proteins).

Suitable emulsifiers are, for example, nonionic surfactants from at least one of the following groups:

(1) products of the addition of 2 to 30 moles of ethylene oxide and/or 0 to 5 moles of propylene oxide onto linear $C_{8-22}$ fatty alcohols, $C_{12-22}$ fatty acids and alkyl phenols containing 8 to 15 carbon atoms in the alkyl group;

(2) $C_{12/18}$ fatty acid monoesters and diesters of adducts of 1 to 30 moles of ethylene oxide with glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) adducts of 15 to 60 moles of ethylene oxide with castor oil and/or hydrogenated castor oil;

(6) polyol esters and, in particular, polyglycerol esters such as, for example, polyglycerol polyricinoleate, polyglycerol poly-12-hydroxy-stearate or polyglycerol dimerate. Mixtures of compounds from several of these dasses are also suitable;

(7) adducts of 2 to 15 moles of ethylene oxide with castor oil and/or hydro-generated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) mono-, di and trialkyl phosphates and mono-, di- and/or tri-PEG-alkyl phosphates and salts thereof;

(10) wool wax alcohols;

(11) polysiloxanepolyalkyl polyether copolymers and corresponding derivatives;

(12) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol or polyglycerol, and

(13) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide andlor propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

$C_{8/18}$ alkyl mono- and oligoglycosides, their production and their use as surfactants are known from the prior-art literature. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

Other suitable emulsifiers are zwitterionic surfactants. Zwitterionic surfactants are surface-active compounds which contain at least one quatemary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazo-lines containing 8 to 18 carbon atoms in the alkyl or acyl group and cocoacyl-aminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one—COOH—or—$SO_3H$—group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. According to the invention, other suitable emulsifiers besides ampholytic surfactants are quaternary emulsifiers, those of the esterquat type, preferably methyl-quatenized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlescing waxes are, for example, alkylene glycol esters, particularly ethylene glycol distearate; fatty acid alkanolamides, particularly cocofatty acid diethanolamide; partial glycerides, particularly stearic acid monoglyceride; esters of polybasic, optionally hydroxysubstituted carboxylic acids with $C_{6-22}$ fatty alcohols, particularly long-chain esters of tartaric acid; fatty compounds such as, for example, fatty alcohols, fatty ketones, fatty aldehydes, fatty ethers and fatty carbonates which contain in all at least 24 carbon atoms, particularly laurone and distearyl ether; fatty acids, such as stearic acid, hydroxystearic acid or behenic acid, ring opening products of $C_{12-22}$ olefin epoxides with $C_{12-22}$ fatty alcohols and/or polyols containing 2 to 15 carbon atoms and 2 to 10 hydroxyl groups and mixtures thereof.

The consistency regulators mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quatemized hydroxyethyl cellulose obtainable from Amerchol under the name of Polymer JR 400®, cationic starch, copolymers of diallyl ammonium salts and acrylamides, quatemized vinyl pyrrolidone/vinyl imidazole polymers such as, for example, Luviquat® (BASF), condensation products of polyglycols and amines, quatemized collagen polypeptides such as, for example, Lauryldimonium Hydroxypropyl Hydrolyzed Collagen (Lamequat® L, Grunau GmbH), quatemized wheat polypeptides, polyethyleneimine, cationic silicone polymers such as, for example, Amidomethicone, copolymers of adipic acid and dimethylaminohy-droxypropyl diethylenetriamine (Cartaretine®, Sandoz AG), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quatemized chitosan, optionally in microcrystalline distribution, condensation products of dihaloalkylene, for example dibromobutane, with bis-dialkylamines, for example bis-dimethylamino-1,3-propane, cationic guar gum such as, for example, Jagua® CBS, Jaguar® C-17, Jaguar® C-16 of Celanese, USA, quatemized ammonium salt polymers such as, for example, Mirapol® A-15, Mirapol® AD-1, Mirapol® AZ-1 of Miranol, USA.

Suitable anionic, zwifterionic, amphoteric and nonionic polymers are, for example, vinyl acetate/crotonic acid copolymers, vinyl pyrrolidone/vinyl acrylate copolymers, vinyl acetate/butyl maleate/isobonyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/terL-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Typical examples of fats are glycerides while suitable waxes are inter alia beeswax, camauba wax, candelilla wax, montan wax, paraffin wax or microwaxes, optionally in combination with hydrophilic waxes, for example cetyl stearyl alcohol or partial glycerides. Metal salts of fatty acids such as, for example, magnesium, aluminium and/or zinc stearate or ricinoleate may be used as stabilizers. In the context of the invention, biogenic agents are, for example, tocopherol, tocopherol acetate, tocopherol palmitate, ascorbic acid, carotene, deoxyribonucleic acid, retinol, bisabolol, allantoin, phytantriol, panthenol, AHA acids, amino acids, ceramides, pseudoceramides, essential oils, plant extracts and vitamin complexes. Climbazol, octopirox and zinc pyrethion may be used as antidandruff agents. Typical film formers are, for example, chitosan, microcrystalline chitosan, quatemized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Montmorillonites, clay minerals, Pemulen and alkyl-modified Carbopol types (Goodrich) may be used as swelling agents for aqueous phases.

UV filters in the context of the invention are, for example, organic substances which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor and derivatives thereof, for example 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester, esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2(-ethylhexyl ester, salicylic acid-4-isopropylbenzyl ester, salicylic acid homomenthyl ester, derivatives of benzophenone, preferably 2-hydroxyf4-methoxybenzophenone, 2-hydroxy-4-methoxy4'-methylbenzophenone, 2,2'-dihydroxy-4-methoxybenzophenone;

esters of benzalmalonic acid, preferably 4-methoxybenzalmalonic acid di-2-ethylhexyl ester, triazine derivatives such as, for example, 2,4,6-trianilino-(p-carbo-2'-ethyl-1'-hexyloxy)-1,3,5-triazine and Octyl Triazone;

propane-1,3-diones such as, for example, 1-(4tert.butylphenyl)-3-(4'-methoxyphenyl)-propane-1,3dione;

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic add derivatives of 3-benzylidene camphor such as, for example, 4-(2-oxo-3-bornylidenemethyl)-benzene sulfonic acid and 2-methyl-5-(2-oxo-3-bornylidene)sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione or 1-phenyl3(4'-isopropylphenyl)-propane-1,3-dione. The UV-A and UV-B filters may of course also be used in the form of mixtures. Besides the soluble substances mentioned, insoluble pigments, i.e. finely dispersed metal oxides or salts, for example titanium dioxide, zinc oxide, iron oxide, aluminium oxide, cerium oxide, zirconium oxide, silicates (talcum), barium sulfate and zinc stearate, may also be used for this purpose. The particles should have an average diameter of less than 100 nm, preferably from 5 to 50 nm and more preferably from 15 to 30 nm. They may be spherical in shape although ellipsoidal partides or other non-spherical particles may also be used. Besides the two above-mentioned groups of primary light filters, secondary light filters of the antioxidant type, which interrupt the photochemical reaction chain initiated when UV radiation penetrates into the skin, may also be used. Typical examples of these secondary light filters are Superoxid-Dismutase, tocopherols (vitamin E) and ascorbic acid (vitamin C). Other suitable Uw filters can be found in P. Finkel's review in S ÖFW-Journal 122, 543 (1996).

In addition, hydrotropes, for example ethanol, isopropyl alcohol or polyols, may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cydovertal, lavendin oil, clary oil, β-damascone, geranium oil bourbon, cyclohexyl salicylate, Vertofix Coeur, Iso-E-super, Fixolide NP, evemyl, iraldein gamma, phenylacetic acid, geranyl acetate, benzyl acetate, rose oxide, romillate, irotyl and floramate.

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be produced by standard hot or cold processes and are preferably produced by the phase inversion temperature method.

EXAMPLES

25% by weight solutions of various nonionic surfactants were prepared at 40° C. and were then evaluated for appearance, their ability to remove decorative cosmetics and their rinse-off behavior with water. Evaluation was subjective on a scale of 1 to 5: (1)=very good, transparent;

(2)=good; (3) =satisfactory, slightly clouded; (4)=adequate, cloudy; (5)=poor, very cloudy. Table 1 shows that ethoxylated partial glycerides are superior to the other nonionic surfactants liquid at room temperature. The solutions are transparent and show better cleansing power and better rinse-off behavior. The quantities used in the Examples are % by weight. Examples 1 to 5 correspond to the invention, Examples C1 to C5 are intended for comparison.

TABLE 1

Aqueous nonionic surfactant solutions

| Nonionic surfactant/ evaluation | 1 | 2 | 3 | 4 | 5 | C1 | C2 | C3 | C4 | C5 |
|---|---|---|---|---|---|---|---|---|---|---|
| PEG-7 Glyceryl Laurate | 25 | — | — | — | — | — | — | — | — | — |
| PEG-7 Glyceryl Cocoate | — | 25 | — | — | — | — | — | — | — | — |
| PEG-10 Glyceryl Cocoate | — | — | 25 | — | — | — | — | — | — | — |
| PEG-10 Glyceryl Isostearate | — | — | — | 25 | — | — | — | — | — | — |
| PEG-20 Glyceryl Cocoate | — | — | — | — | 25 | — | — | — | — | — |
| PEG-20 Hydrogenated Castor Oil | — | — | — | — | — | 25 | — | — | — | — |
| PEG-40 Sorbitan Monooleate | — | — | — | — | — | — | 25 | — | — | — |
| PEG-20 Sorbitan Monostearate | — | — | — | — | — | — | — | 25 | — | — |
| PEG-30 Sorbitan Tetraoleate | — | — | — | — | — | — | — | — | 25 | — |
| PEG-12 Monostearate | — | — | — | — | — | — | — | — | — | 25 |
| Water | | | | | to 100 | | | | | |
| Appearance (20° C.) | 1 | 1 | 1 | 1 | 1 | 4 | 1 | 4 | 4 | 1 |
| Cleansing performance | 1 | 1 | 1 | 2 | 2 | 5 | 3 | 5 | 5 | 3 |
| Rinse-off behavior | 1 | 1 | 1 | 2 | 2 | 5 | 3 | 5 | 5 | 2 |

The ingredients listed in Table 2 were mixed together at 70° C. and then cooled with stirring to around 20° C. Transparent face cleansers were obtained and were evaluated on the same scale as in Table 1. The cleansers according to the invention are transparent, are distinguished by a pleasant feel and show excellent cleansing performance and rinse-off behavior. Examples 6 to 11 correspond to the invention while Examples C6 to C9 are for comparison.

TABLE 2

Cosmetic formulations

| Nonionic surfactant/ evaluation | 6 | 7 | 8 | 9 | 10 | 11 | C6 | C7 | C8 | C9 |
|---|---|---|---|---|---|---|---|---|---|---|
| PEG-7 Glyceryl Cocoate | 25 | 50 | 50 | 40 | 30 | 20 | 5 | 10 | 15 | 10 |
| 2-Ethylhexylic Glycerides | 5 | — | — | — | — | — | — | — | — | — |
| Octyl dodecanol | — | 20 | — | — | — | — | — | — | — | — |
| Paraffin, liquid | — | — | 50 | 60 | 70 | 80 | — | — | — | 90 |
| Water | | | | | to 100 | | | | | |
| Appearance (20° C.) | 1 | 1 | 1 | 1 | 1 | 1 | 3 | 3 | 3 | 1 |
| Cleansing performance | 1 | 1 | 1 | 1 | 1 | 1 | 4 | 3 | 1 | 2 |
| Rinse-off behavior | 1 | 1 | 1 | 1 | 1 | 2 | 4 | 3 | 3 | 3 |

Formulations Examples.

The ingredients of the following formulations were melted by heating and stirred. After cooling, transparent formulations were obtained. Since the face cleanser is a liquid formulation, it even enables dirt deeply ingrained in the skin to be dispersed or dissolved. After cleaning, the formulation can easily be rinsed off with water and the skin feels fresh. The quantities shown are % by weight, water to 100% by weight.

| Face cleanser | |
|---|---|
| PEG-7 Glyceryl Laurate | 25.0 |
| 2-Ethylhexylic Glycerides | 5.0 |
| 1,3-Butanediol | 7.0 |
| Parabens | 1.0 |
| Sun protection lotion | |
| PEG-7 Glyceryl Stearate | 20.0 |
| Hydrogenated Palm Glycerides | 8.0 |
| Octyl Methoxycinnamate | 5.0 |
| 4-Methylbenzylidene Camphor | 3.0 |
| 3-Benzophenone | 4.0 |
| Titanium dioxide | 1.0 |
| Zinc oxide | 1.0 |
| Octyl Triazone | 1.0 |
| Glycerol (86% by weight) | 5.0 |

What is claimed is:

1. A cosmetic formulation comprising:
    (a) from about 20% to about 80% by weight of a mixture of ethoxylated monoglycerides and diglycerides of the general formula (I):

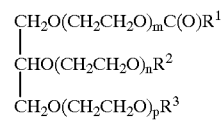

wherein $R^1C(O)$— represents a linear or branched, saturated or unsaturated acyl group having from about 6 to about 22 carbon atoms, each of $R^2$ and $R^3$ independently represents a hydroxyl moiety or $R^1C(O)$—, with the proviso that at least one of $R^2$ and $R^3$ is a hydroxyl moiety, and m+n+p equals a number of from about 1 to about 100, wherein the mixture comprises from about 50% to about 95% by weight monoglycerides; and
    (b) up to about 80% by weight an oil component; the balance of said formultaion comprising one or more additional components selected from water, cosmetic auxiliaries and cosmetic additives.

2. The cosmetic formulation according to claim 1, wherein the one or more ethoxylated partial glycerides are present in an amount of from about 25% to about 35% by weight.

3. The cosmetic formulation according to claim 2, wherein the oil component is present in an amount of from about 15% to about 75% by weight.

4. The cosmetic formulation according to claim 1, wherein $R^1C(O)$—represents a linear or branched, saturated or unsaturated acyl group having from about 12 to about 18 carbon atoms and m+n+p equals a number of from about 5 to about 10.

5. The cosmetic formulation according to claim 2, wherein $R^1C(O)$— represents a linear or branched, saturated or unsaturated acyl group having from about 12 to about 18 carbon atoms and m+n+p equals a number of from about 5 to about 10.

6. The cosmetic formulation according to claim 3, wherein $R^1C(O)$— represents a linear or branched, saturated or unsaturated acyl group having from about 12 to about 18 carbon atoms and m+n+p equals a number of from about 5 to about 10.

7. The cosmetic formulation according to claim 1, wherein the mixture comprises from about 60% to 90% by weight monoglycerides.

8. The cosmetic formulation according to claim 4, wherein m+n+p equals about 7.

9. The cosmetic formulation according to claim 7, wherein $R^1C(O)$— represents a linear or branched, saturated or unsaturated acyl group having from about 12 to about 18 carbon atoms and m+n+p equals a number of from about 5 to about 10.

10. The cosmetic formulation according to claim 9, wherein m+n+p equals about 7.

11. The cosmetic formulation according to claim 1, further comprising at least one UV filter composition.

12. A method of removing decorative makeup from skin, said method comprising, applying to an area of skin having decorative makeup to be removed, a formulation comprising:
(a) from about 20% to about 80% by weight of one or more ethoxylated partial glycerides of the general formula (I):

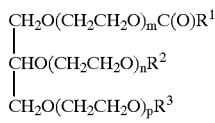

wherein $R^1C(O)$— represents a linear or branched, saturated or unsaturated acyl group having from about 6 to about 22 carbon at moiety or $R^1C(O)$—, with the proviso that at least one of $R^2$ and $R^3$ is a hydroxyl moiety, and m+n+p equals a number of from about 1 to about 100; and
(b) up to about 80% by weight an oil component; the balance of said formulation comprising one or more additional components selected from water, cosmetic auxiliaries and cosmetic additives.

13. The method according to claim 12, wherein the one or more ethoxylated partial glycerides are present in an amount of from about 25% to about 35% by weight, and wherein the oil component is present in an amount of from about 15% to about 75% by weight.

14. The method according to claim 12, wherein $R^1C(O)$— represents a linear or branched, saturated or unsaturated acyl group having from about 12 to about 18 carbon atoms and m+n+p equals a number of from about 5 to out 10.

15. The method according to claim 12, wherein the one or more ethoxylated partial glycerides of the general formula (I) comprise a mixture of monoglycerides and diglycerides, and wherein the comprises from about 50% to about 95% by weight monoglycerides.

16. The method according to claim 15, wherein the mixture comprises from about 60% to about 90% by weight monoglycerides.

17. A method of removing decorative makeup from skin, said method comprising: applying to an area of skin having decorative makeup to be removed, a formulation comprising:
(a) from about 20% to about 80% by weight of a mixture of ethoxylated monoglycerides and diglycerides of the general formula (I):

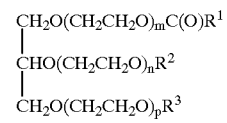

wherein $R^1C(O)$— represents a linear or branched, saturated or unsaturated acyl group having from about 6 to about 22 carbon atoms, each of $R^2$ and $R^3$ independently represents a hydroxyl moiety or $R^1C(O$—, with the proviso that at least one of $R^2$ and $R^3$ is a hydroxyl moiety, and m+n+p equals a number of from about 1 to about 100, wherein the mixture comprises from about 50% to about 95% by weigh monoglycerides; and
(b) up to about 80% by weight an oil component; the balance of said formulation comprising one or more additional components selected from water, cosmetic auxiliaries and cosmetic additives.

18. The method according to claim 17, wherein the mixture of ethoxylated monoglycerides and diglycerides are present in an amount of from about 25% to about 35% by weight, and wherein the oil component is present in an amount of from about 15% to about 75% by weight.

19. The method according to claim 17, wherein $R^1C(O)$— represents a linear or branched, saturated or unsaturated acyl group having from about 12 to about 18 carbon atoms and m+n+p equals a number of from about 5 to about 10.

20. The method according to claim 17, wherein the mixture comprises from about 60% to about 90% by weight monoglycerides.

* * * * *